United States Patent
Fujioka et al.

[11] Patent Number: 5,846,231
[45] Date of Patent: Dec. 8, 1998

[54] DISPOSABLE ABSORBENT ARTICLE

[75] Inventors: Yoshihisa Fujioka, Kagawa-ken; Rumi Yamaki, Ehime-ken, both of Japan

[73] Assignee: Uni-Charm Corporation, Ehime-ken, Japan

[21] Appl. No.: 698,535

[22] Filed: Aug. 15, 1996

[30] Foreign Application Priority Data

Aug. 15, 1995 [JP] Japan .................................. 7-208237

[51] Int. Cl.$^6$ ................................................ A61F 13/15
[52] U.S. Cl. ......................................... 604/380; 604/385.1
[58] Field of Search .............................. 604/378–380, 604/358, 385.1

[56] References Cited

U.S. PATENT DOCUMENTS

| 2,788,003 | 4/1957 | Morin ....................................... 604/380 |
| 2,834,703 | 5/1958 | Atkinson ................................... 604/378 |
| 3,028,783 | 12/1962 | Taylor . |
| 4,443,512 | 4/1984 | Delvaux ..................................... 604/379 |
| 4,449,979 | 5/1984 | Holtman ..................................... 604/379 |
| 4,892,535 | 1/1990 | Bjornberg et al. ......................... 604/380 |
| 5,151,091 | 9/1992 | Glaug et al. ............................. 604/385.1 |
| 5,578,024 | 11/1996 | Mizutani et al. ......................... 604/380 |

FOREIGN PATENT DOCUMENTS

| 0 067 916 | 12/1982 | European Pat. Off. . |
| 3205931 A1 | 9/1983 | Germany . |
| 1-141707 | 9/1989 | Japan . |
| 2-84623 | 7/1990 | Japan . |
| 2 105592 | 3/1982 | United Kingdom . |

*Primary Examiner*—Mark O. Polutta
*Attorney, Agent, or Firm*—Lowe Hauptman Gopstein Gilman & Berner

[57] ABSTRACT

A disposable absorbent article according to the invention comprises a liquid-absorbent core provided intermittently in longitudinal and transverse directions thereof with a plurality of linear slits extending therethrough extending longitudinally of the article and thereby promote spread of body fluids.

8 Claims, 2 Drawing Sheets

DISPOSABLE ABSORBENT ARTICLE

BACKGROUND OF THE INVENTION

The present invention relates to a disposable absorbent article and more particularly to an absorbent article such as a disposable diaper, an incontinence pad, a menstruation napkin and the like for absorption and containment of body fluids.

Japanese Laid-Open Utility Model Application No. Hei1-141707 discloses a disposable diaper comprising a liquid-absorbent core divided into several pieces spaced from one another so that top- and backsheets covering the core are bonded to each other between each pair of the adjacent pieces. Japanese Laid-Open Utility Model Application No. Hei2-84623 discloses a disposable diaper comprising a liquid-absorbent core provided with linear slits extending through a thickness of the core and extending longitudinally of the core so that top- and backsheets covering the core are bonded to each other along these linear slits.

In the arrangement disclosed in the aforesaid Application No. Hei1-141707, a region of the core lying in a crotch zone of the diaper is soon saturated with body discharged predominantly onto this region and undesirable leakage of body fluids begins before the other region is more or less saturated with body fluids, since body fluids can not spread from one piece to another piece of the divided core. In the arrangement disclosed in the aforesaid Application No. Hei2-84623, effective use of a total width of the core in the crotch zone is difficult, since body exudates can spread longitudinally of the diaper but can not spread transversely of the diaper. Consequently, the middle region of the core lying in the crotch zone may be soon saturated with body fluids before side edge regions of the core lying in transversely opposite regions of the crotch zone and may give the wearer a significant wet feeling.

SUMMARY OF THE INVENTION

In view of such problem, it is a principal object of the invention to provide a disposable absorbent article so improved that a high diffusivity is assured even when a liquid-absorbent core is provided with linear slits extending longitudinally of the article and the core is held against shifting aside during use of the article.

The object set forth above is achieved, according to the invention, by a disposable absorbent article comprising a liquid-permeable topsheet, a liquid-impermeable backsheet and a liquid-absorbent core disposed between these two sheets and extending longitudinally of the article, wherein the absorbent core is provided intermittently in longitudinal and transverse directions thereof a plurality of linear slits extending therethrough longitudinally of the article so that the topsheet and the backsheet are integrally bonded to each other along the linear slits to form linear grooves extending along the linear slits.

Preferably, the absorbent core contains a hydrophilic fibrous material of at least 50% by weight and a density of the fibrous material contained in each interrupted region defined between each pair of adjacent ends of the longitudinally aligned linear slits is adjusted to be higher than a density of the fibrous material contained in the remaining region of the core.

Preferably, the density of the fibrous material contained in the core is adjusted to be higher along a side edge region having a width of at least 2 mm of each core section defined by each pair of the linear slits being transversely adjacent to each other than the density in the remaining region of this core section.

DESCRIPTION OF THE PREFERRED EMBODIMENTS

Figure 1:
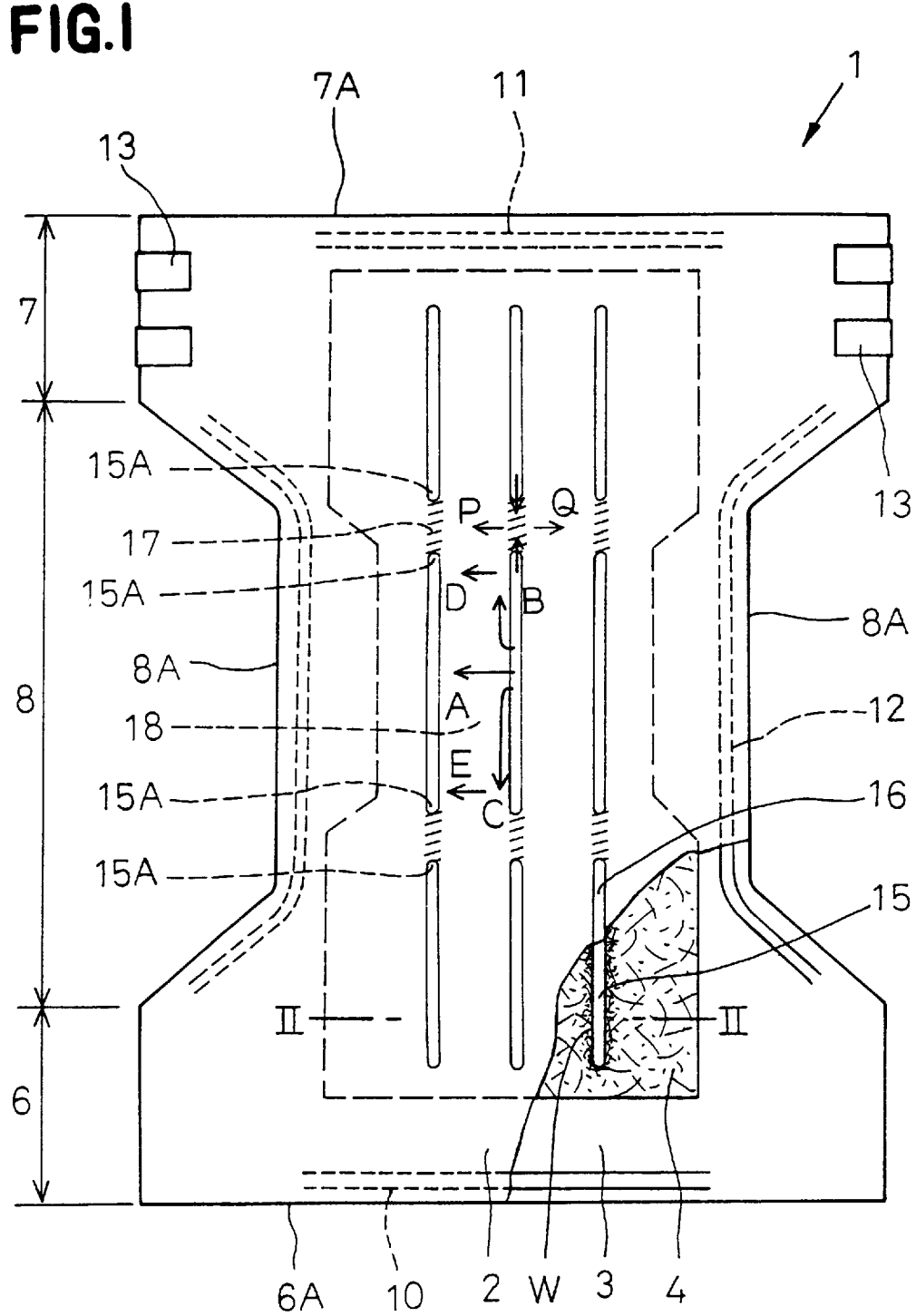
FIG. 1 is a plan view showing an embodiment of the invention in the form of disposable diaper as partially broken away.

Referring to FIG. 1 which is a plan view as partially broken away, a diaper 1 comprises a liquid-permeable topsheet 2, a liquid-impermeable backsheet 3 and a liquid-absorbent core 4 disposed between these two sheets 2, 3 and extending longitudinally of them from the viewpoint of its components and is longitudinally composed of a front waist region 6, a rear waist region 7 and a crotch region 8 interposed between these two regions 6, 7. The topsheet 2 and the backsheet 3 extend outward beyond a peripheral edge of the core 4 and have their inner surfaces water-tightly bonded to each other at their outward extensions. The front and rear waist regions 6, 7 are provided along their longitudinally outer ends 6A, 7A with elastic members 10, 11 bonded in a stretched condition to an inner surface of at least one of the topsheet 2 and the backsheet 3 so as to surround together a wearer's waist and the crotch region 8 is provided along its transversely opposite side edges 8A with elastic members 12 also bonded in a stretched condition to an inner surface of at least one of the topsheet 2 and the backsheet 3 so as to surround a wearer's respective legs. The rear waist zone region is provided at its transversely opposite side edges with tape fasteners 13 attached thereto. The core 4 is formed longitudinally as well as transversely thereof with a plurality of intermittently aligned slits 15.

Figure 2:
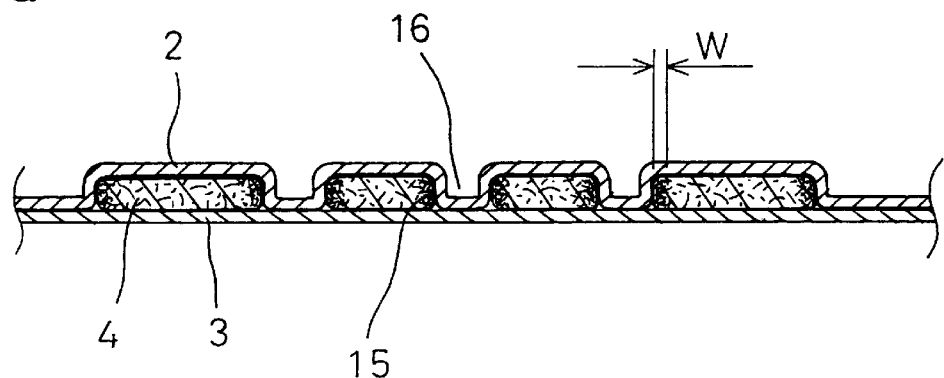
FIG. 2 is a sectional view taken along a line II—II in FIG. 1.

Now referring to FIG. 2 which is a sectional view taken along a line II—II in FIG. 1, the linear slits 15 define a gaps extending through the core 4. Along them, the topsheet 2 is curved downward until it comes in direct contact with the backsheet 3 and is integrally bonded to the backsheet 3 so as to form a plurality of linear grooves 16 each having a width of about 1 to 15 mm, preferably of about 2 to 10 mm and its inner wall being defined by the topsheet 2.

The core 4 contains a hydrophilic fibrous material of at least 50% by weight. While it is preferred to use wood pulp fibers as such material, the other natural or regenerated fibrous materials may be effectively used. The core may further contain the other materials such as discrete particles of a water insolate polymeric hydrogel or hydrophobic thermoplastic synthetic fibers up to 50% by weight. Referring to the sectional view of FIG. 2, a density of the hydrophilic fibrous material in the core 4 is adjusted to be higher in its side edge region W having a width of at least 2 mm, preferably in its peripheral region than the remaining region of each section defined by a pair of adjacent linear slits 15. More specifically, the density is adjusted to be progressively decreased from said side edge to the middle of said core section. Referring to FIG. 1, the density is adjusted to be higher along interrupted regions 17 (indicated by oblique lines) defined between respective pairs of ends 15A of the longitudinally aligned linear slits 15 than along the other regions, for example, in said core sections opposed to each other across each of the interrupted region 17. The density in each interrupted region 17 is preferably adjusted to be higher than the density in the side edge region W, but may be substantially the same as the latter.

With the diaper 1 constructed as described, the topsheet 2 and the backsheet 3 are bonded to each other along the respective linear slits 15 and therefore it is unnecessary to bond the core 4 to the topsheet 2 and/or the backsheet 3 without any apprehension that the core 4 might shift during use of the diaper 1. Body fluids such as urine flowing into the linear grooves 16 first spreads longitudinally of the diaper 1. The body fluids generally tend to spread from the regions in which the density of the fibrous material is relatively high toward the regions in which the density of the fibrous material is relatively low and tend to spread more rapidly in the regions in which the density is relatively high than in the regions in which the density is relatively low. Consequently, the body fluids received by the linear grooves 16 spread inward into the core 4 as indicated by an arrow A and, in the peripheral regions W of the linear slits 15 along which the density of the fibrous material is relatively high, the body fluids rapidly spread longitudinally of the diaper 1 as indicated by arrows B, C. Also after such spreading, the body fluids spread inward into the core 4 as indicated by arrows D, E. In the proximity of each end 15A, the body fluids rapidly spread into the adjacent interrupted region 17 containing the fibrous material at a relatively high density and further spread from the interrupted region 17 transversely of the diaper 1 as indicated by arrows P, Q. In this manner, the presence of the peripheral regions W as well as the interrupted regions 17 both containing the fibrous material at relatively high densities allows the body fluids discharged onto the crotch region 8 to spread longitudinally as well as transversely without staying there and thereby alleviates an undesirable wet feeling of the crotch region 8. The presence of the interrupted regions 17 particularly allows the body fluids to rapidly spread transversely of the diaper 1 and thereby allows a total width of the core 4 to be effectively used although the core 4 is provided with the linear slits 15 which might otherwise tend to prevent the body fluids from spreading transversely of the core 4.

Figure 3:
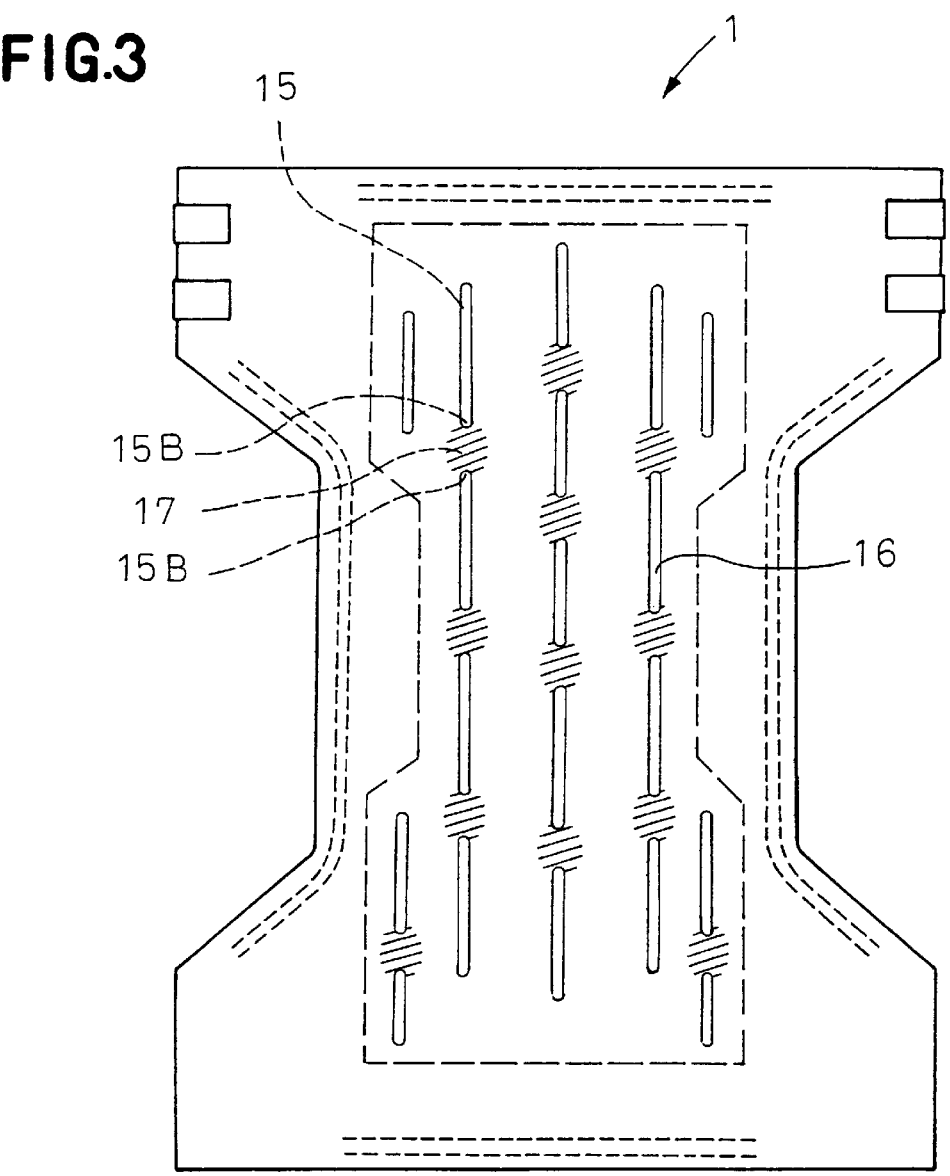
FIG. 3 is a plan view showing a variant of the diaper shown by FIG. 1.

FIG. 3 is a view similar to FIG. 1 but showing a variant in arrangement of the linear slits 15 and the linear grooves 16. The linear slits 15 are intermittently arranged so as to be aligned with one another longitudinally of the core 4, but the interrupted regions 17 provided in respective pair of adjacent linear slits 15 are not in mutual alignment transversely of the core 4. Also in this variant, the interrupted regions 17 indicated by oblique lines contain the fibrous material at a density higher than the other regions.

In order to further promote spread of the body fluids in the diaper 1, the density of the fibrous material contained in the core 4 may be adjusted to be progressively increased from the crotch region 8 toward the front and rear waist regions 6, 7. Alternatively, any suitable agent increasing a hydrophilicity (surfactant) may be applied to the linear grooves 16 or tape-like sheet strips having a high diffusing ability may be interposed between the topsheet 2 and the backsheet 3 in the respective linear grooves 16.

Components of the diaper 1 may be made of the materials conventionally used in the field of disposable diaper. For example, the topsheet 2 may be made of a nonwoven fabric or a perforated plastic film, the backsheet 3 may be made of a plastic film such as polyethylene and the core 4 may be made of the previously described shaped fibrous material. To adjust the density of the fibrous material in the core 4, a weight per unit area of pulp fibers may be partially changed while a shaping pressure is maintained at a constant level or inversely the shaping pressure may be partially changed while the weight per unit area is maintained at a constant level. Bonding of various components such as the topsheet 2 and the backsheet 3 may be achieved by using adhesive such as hot melt adhesive and heat-sealing technique for heat-sealable materials. The diaper 1 is not limited to the open type as shown and the invention is applicable to the pants type diaper formed by bonding the front and rear waist regions along their transversely opposite side edges.

The article according to the invention allows the body exudates predominantly discharged onto the crotch region, in the respective linear slits, to readily spread longitudinally of the article and allows, in the interrupted regions between the linear slits longitudinally aligned with one another, to spread transversely of the article, since the core is formed with the linear slits extending longitudinally of the article, these linear slits are intermittently arranged longitudinally as well as transversely and the topsheet and the backsheet are bonded to each other along the respective linear slits so as to form the linear grooves. The density of the hydrophilic fibrous material contained in the interrupted regions defined between respective pairs of adjacent longitudinal ends of the linear slits may be adjusted to be relatively high in order to promote spread of the body fluids in longitudinal direction as well as in the transverse direction of the core. The density of the fibrous material contained in each core sections defined by each pair of adjacent linear slits may be adjusted to be higher along the side edge region of this core section than in the remaining region of the same core section in order to further promote spread of the body fluids longitudinally along said side edge region. In this manner, the article according to the invention allows a liquid-absorbent ability of the core in its transverse direction to be effectively used in spite of the presence of the longitudinal linear slits and thereby an undesirable wet feeling of the crotch region.

Furthermore, the core is prevented by the topsheet and the backsheet bonded to each other so as to for the respective linear grooves from shifting longitudinally as well as transversely. As a result, there is no apprehension that the core might be moved aside to cluster, thereby give a wearer an unpleasant feeling or deteriorate a desired absorbing ability for excretion.

What is claims is :

1. A disposable absorbent article comprising a liquid permeable topsheet, a liquid-impermeable backsheet and a liquid-absorbent core disposed between and extending longitudinally of said topsheet and said backsheet, wherein said core is provided intermittently in longitudinal and transverse directions thereof with a plurality of slits extending therethrough longitudinally of said article so that said topsheet and said backsheet are fixedly bonded to each other along said slits to form grooves extending along said slits, and wherein said core contains a hydrophilic fibrous material and a density of said fibrous material contained in an interrupted region defined between at least one pair of adjacent ends of the longitudinally aligned slits is adjusted to be higher than a density of said fibrous material contained in side edge regions of said core extending along said slits in areas of said core located between transversely spaced slits.

2. The article as defined by claim 1, wherein said core contains hydrophilic fibrous material of at least 50% by weight.

3. The article as defined by claim 1, wherein the density of the fibrous material contained in said core is adjusted to be higher along the side edge regions having a width of at least 2 mm of each core section.

4. The article as defined by claim 3, wherein the density in each interrupted region is adjusted to be higher than the density in the side edge region of each said core section defined by each pair of said linear slits.

5. The article as defined by claim 1, wherein the density of the fibrous material contained in said core is adjusted to be higher along a side edge region of each slit, said side edge region having a width of at least 2 mm , than the density of the fibrous material in a remaining region of each core section located transversely between a transverse spaced Pair of said slits.

6. The article as defined by claim 5, wherein the density of the fibrous material contained in said core is adjusted to be progressively decreased from the side edge region of each slit core section to a middle of said core section defined between each pair of said slits.

7. The article as defined by claim 1, wherein said slits are linear and said grooves are linear.

8. A disposable absorbent article comprising a liquid permeable topsheet, a liquid-impermeable backsheet and a liquid-absorbent core disposed between and extending longitudinally of said topsheet and said backsheet, wherein said core is provided intermittently in longitudinal and transverse directions thereof with a plurality of slits extending therethrough longitudinally of said article so that said topsheet and said backsheet are fixedly bonded to each other along said slits to form grooves extending along said slits, and wherein said core contains a plurality of core sections having a hydrophilic fibrous material, a density of the fibrous material contained in said core progressively decreases from a side edge region of each said core section defined by each pair of said slits to a middle of said core section located between a transverse spaced pair of said slits.

\* \* \* \* \*